(12) United States Patent
Nakano et al.

(10) Patent No.: US 7,983,466 B2
(45) Date of Patent: Jul. 19, 2011

(54) MICROSCOPE APPARATUS AND CELL OBSERVATION METHOD

(75) Inventors: Mitsuhiro Nakano, Hachioji (JP); Tatsuo Nakata, Hino (JP)

(73) Assignee: Olympus Corporation, Tokyo (JP)

( * ) Notice: Subject to any disclaimer, the term of this patent is extended or adjusted under 35 U.S.C. 154(b) by 1020 days.

(21) Appl. No.: 11/800,119

(22) Filed: May 4, 2007

(65) Prior Publication Data

US 2007/0269796 A1  Nov. 22, 2007

(30) Foreign Application Priority Data

May 18, 2006  (JP) ................................. 2006-138848

(51) Int. Cl.
*G06K 9/00* (2006.01)
(52) U.S. Cl. .............................. 382/133; 382/128; 435/4
(58) Field of Classification Search .................. 382/133
See application file for complete search history.

(56) References Cited

U.S. PATENT DOCUMENTS

| 6,094,300 | A | 7/2000 | Kashima et al. |
|---|---|---|---|
| 2003/0161515 | A1 | 8/2003 | Salmon et al. |
| 2003/0197924 | A1 | 10/2003 | Nakata |
| 2005/0122579 | A1 | 6/2005 | Sasaki |
| 2005/0256654 | A1 | 11/2005 | Salmon et al. |
| 2005/0283317 | A1* | 12/2005 | Vaisberg et al. ................ 702/19 |
| 2007/0139753 | A1 | 6/2007 | Nakata |

FOREIGN PATENT DOCUMENTS

| EP | 1 146 480 A1 | 10/2001 |
|---|---|---|
| JP | 2000-097857 A | 4/2000 |

* cited by examiner

*Primary Examiner* — Samir A Ahmed
*Assistant Examiner* — Ruiping Li
(74) *Attorney, Agent, or Firm* — Holtz, Holtz, Goodman & Chick, PC

(57) ABSTRACT

The invention provides a microscope apparatus, used for identifying the cell phases of a plurality of cells mounted on a stage, including an analysis/observation optical system used for acquiring an observed-image of the cells and a stimulus optical system used for applying an optical stimulus to prescribed cells. Using these optical systems, the cell phases of the cells mounted on the stage are identified, an optical stimulus is applied to the cells, and the state of the cells before and after applying the stimulus is observed.

13 Claims, 8 Drawing Sheets

| INPUT BOX | |
|---|---|
| CELL PHASE | ☐ M FINAL PHASE<br>☐ G1 PHASE<br>☐ S PHASE<br>☐ G2 PHASE<br>☑ M PHASE<br>☐ ALL |

MICROSCOPE APPARATUS AND CELL OBSERVATION METHOD

BACKGROUND OF THE INVENTION

1. Field of the Invention

The present invention relates to microscope apparatuses, and more particularly, to a microscope apparatus and a cell observation method in which it is possible to identify the phase of a cell in the cell cycle and in which an optical stimulus can be applied to a cell.

This application is based on Japanese Patent Application No. 2006-138848, the content of which is incorporated herein by reference.

2. Description of Related Art

A known laser scanning cytometer (LSC) in the related art analyzes the cell phase of a specimen by obtaining image information by irradiating the specimen with laser light and acquiring the resulting fluorescence emitted from the specimen.

In addition, a known laser microscope in the related art has a confocal laser-scanning microscope (CLSM) function enabling it to observe cells identified as being in each phase of the cell cycle (for example, see Japanese Unexamined Patent Application, Publication No. 2000-97857).

This laser microscope includes beam-diameter switching means capable of switching the beam diameter of a laser beam incident on the pupil of an objective lens from a laser light source and light-path switching means for switching the fluorescence generated in the specimen between an observation light path and a light path used for analyzing the cell phase analysis. By switching the beam diameter irradiating the specimen and the light path along which the generated fluorescence travels, both cell-phase analysis and observation of the specimen are performed with a single apparatus.

It is sometimes necessary to observe what kind of activity the cells exhibit in each cell phase, for example, the relationship between the cell phase and the reaction to a stimulus (its effect on the cell). However, the conventional laser microscope described above does not consider such observation.

BRIEF SUMMARY OF THE INVENTION

The present invention provides a microscope apparatus and a cell observation method in which it is possible to rapidly and efficiently observe cell states related to cell phases.

A first aspect of the present invention is a cell observation method comprising a cell-phase identifying step of identifying cell phases of cells; an optical stimulation step of applying an optical stimulus to the cells; and an observed-image acquisition step of acquiring an observed image of the cells.

According to this method, the state of the cells is observed by identifying the cell phases of the cells in the cell-phase identifying step, applying the optical stimulus to the cells in the optical stimulus step, acquiring the observed image of the cells in the observed-image acquisition step, and displaying it on the monitor. In this case, because the method includes the optical stimulus step of applying the optical stimulus to the cells, it is possible to artificially apply the stimulus to the cells. Accordingly, by applying the desired optical stimulus, it is possible to stimulate or arrest the cell activity.

The cell observation method described above may further comprise a storing step of storing a position of each cell and the cell phase thereof in association with each other; an inputting step for specifying a target cell phase for the optical stimulation; and a cell identifying step of identifying positions of the cells in the specified cell phase using information stored in the storing step, wherein, in the optical stimulation step, the optical stimulation is performed at the identified positions.

According to this method, when the cell phase of each cell is identified in the cell-phase identifying process, the cell phase and the position of that cell are stored in association with each other. Thus, when the cell phase to which the optical stimulus is to be applied is specified, the positions of the cells in the specified phase are selected based on the stored information, and optical stimulation is performed only at those cell positions. Accordingly, it is possible to apply the optical stimulus only to cells in a desired cell phase, which enables the behavior due to the optical stimulus to be observed.

The cell observation method described above may further comprise an inputting step for specifying a target cell for the optical stimulation, wherein, in the optical stimulation step, the optical stimulation is performed at the specified cell.

Because the target cell for the optical stimulus is specified, it is possible to selectively apply the optical stimulus to the desired cell.

In the cell observation method described above, in the cell-phase identifying step, illumination light for exciting fluorescence may be radiated to a plurality of the cells, fluorescence generated by the cells by irradiation with the illumination light may be detected, and the cell phase of each cell may be identified by statistically process the brightness of the fluorescence.

According to this method, the cell phase of each cell is identified by irradiating the cells with illumination light for exciting fluorescence, detecting the fluorescence excited at a surface of the cells irradiated with the irradiation light, and statistically processing the detected fluorescence brightness.

A second aspect of the present invention is a microscope apparatus comprising a cell-phase identifying unit configured to identify cell phases of cells; an optical stimulus unit configured to apply an optical stimulus to the cells; and an observed-image acquisition unit configured to acquire an observed image of the cells.

With this configuration, the behavior of the cells is observed by identifying the cell phases of the cells with the cell-phase identifying unit, applying the optical stimulus to the cells with the optical stimulus unit, acquiring the observed image of the cells with the observed-image acquisition unit, and displaying it on the monitor. In this case, because the optical stimulus unit is provided, it is possible to artificially apply a stimulus to the cells. Accordingly, by applying the desired stimulus, it is possible to stimulate or arrest the cell activity.

The microscope apparatus described above may further comprise a storage unit configured to store a position of each cell and the cell phase thereof in association with each other; an input unit configured to specify a target cell phase for the optical stimulus; and a cell-identifying unit configured to identify positions of the cells in the specified cell phase using information stored in the storage unit, wherein the optical stimulus unit performs optical stimulation at the cell positions identified by the cell identifying unit.

According to this configuration, when the cell phase of each cell is identified by the cell-phase identifying unit, the call phase and the cell position are stored in the storage unit in association with each other. Thus, when the target cell phase for the optical stimulus is specified using the input unit, the positions of the cells in that specified cell phase are selected based on the information stored in the storage unit, and optical stimulation is performed only at those cell positions.

Accordingly, it is possible to selectively apply the optical stimulus to cells in the desired cell phase.

The microscope apparatus described above may further comprise an input unit configured to input a position of a target cell for the optical stimulus, wherein the optical stimulus unit performs optical stimulation at the input position.

With this configuration, when the target cell for the optical stimulus is specified using the input unit, optical stimulation is performed at the specified cell. Thus, it is possible to selectively apply the optical stimulus at the desired cell.

In the microscope apparatus described above, the cell-phase identifying unit may include a light-radiating optical system configured to radiate illumination light for exciting fluorescence in a plurality of the cells; a light-detecting unit configured to detect fluorescence generated by the cells due to irradiation with the illumination light; and a cell-phase analyzing unit configured to identify the cell phase of each cell by statistically processing the brightness of the detected fluorescence.

With this configuration, the cell phase of each cell is identified by irradiating the cells with the illumination light for exciting fluorescence, using the irradiation optical system; detecting the fluorescence excited in the cell at the surface irradiated with the irradiation light, using the light detecting unit; and statistically processing the detected fluorescence brightness, using the cell-phase analyzing unit.

The present invention affords an advantage in that it is possible to rapidly and efficiently observe the cell state related to the cell phase.

DETAILED DESCRIPTION OF THE INVENTION

Microscope apparatuses according to embodiments of the present invention will be described below with reference to the drawings.

First Embodiment

A microscope apparatus A according to a first embodiment of the present invention will be described below with reference to the drawings.

Figure 1:
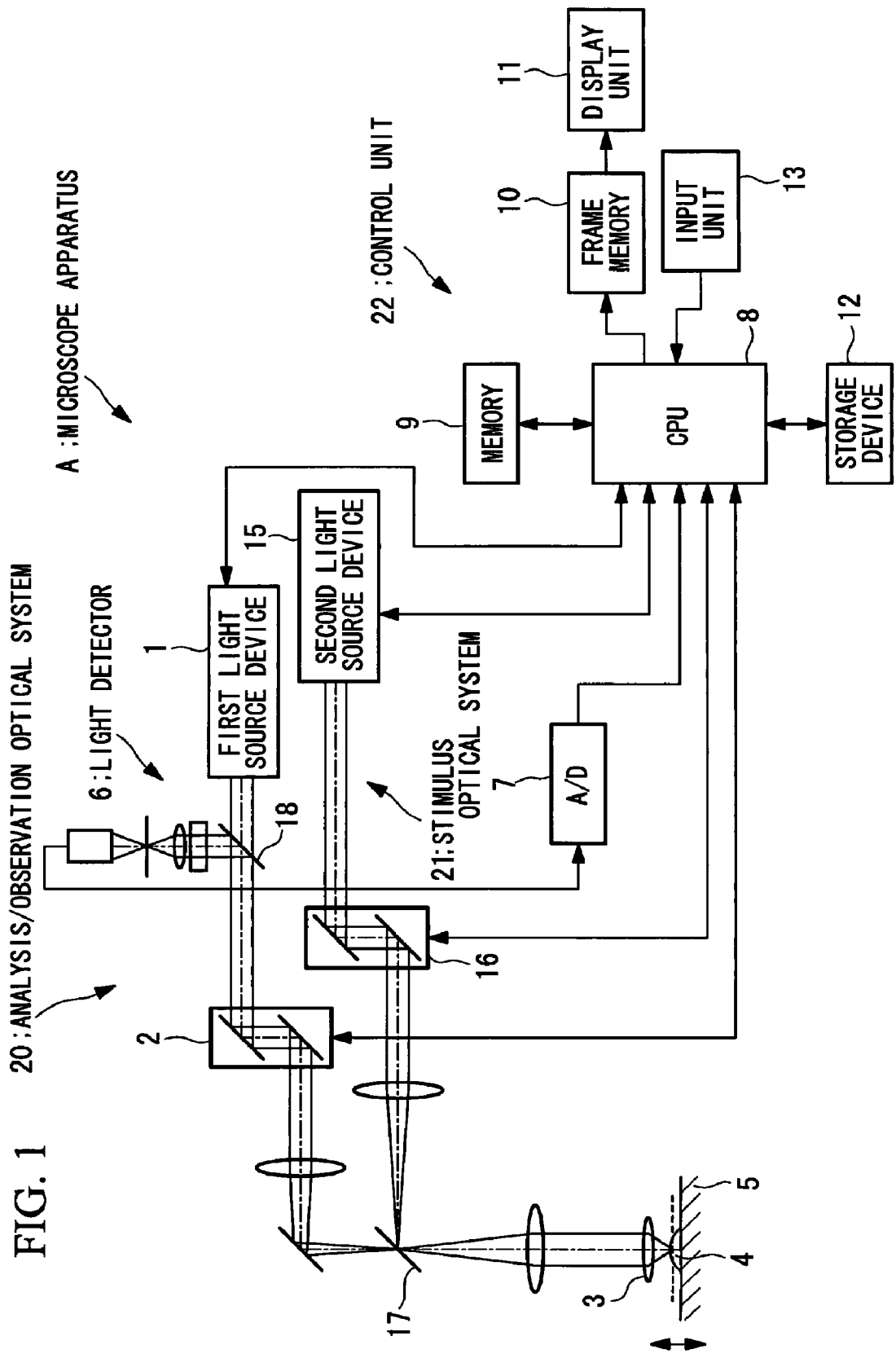
FIG. 1 is a diagram showing the overall configuration of a microscope apparatus according to a first embodiment of the present invention.

The microscope apparatus A according to this embodiment is a laser scanning microscope. In FIG. 1, optical components such as various lenses and pinholes have been appropriately omitted to simplify the description.

As shown in FIG. 1, the microscope apparatus A according to this embodiment includes an analysis/observation optical system 20 and a stimulus optical system 21. The analysis/observation optical system 20 is used for identifying the cell phases of a plurality of cells mounted on a stage 5, as well as for acquiring an observed image of the cells. The stimulus optical system 21 is used for applying an optical stimulus to a prescribed cell.

The analysis/observation optical system 20 includes a first light source device 1 for selectively emitting analysis laser light for identifying the cell phase or observation laser light for observing a cell (hereinafter simply referred to as "first laser light") and a first scanner (scanning unit) 2 for two-dimensionally scanning the first laser light emitted from the first light source device 1 in directions intersecting the optical axis.

For more details of the configuration of the analysis/observation optical system 20, refer to the configuration of the scanning cytometer disclosed, for example, in Japanese Unexamined Patent Application, Publication No. 2000-97857.

The stimulus optical system 21 includes a second light source device 15 for emitting optical stimulus laser light (hereinafter referred to as "second laser light") and a second scanner (deflecting unit) 16 for two-dimensionally scanning the second laser light emitted from the second light source device 15 in directions intersecting the optical axis.

The microscope apparatus A further includes a dichroic mirror (combining unit) 17 for multiplexing the first laser light and the second laser light; an objective lens 3 for focusing the multiplexed first laser light and the second laser light to irradiate a cell, as well as for collecting fluorescence generated when a fluorescent substance in the cell is excited upon irradiating the cell with the laser light used for illumination; and a light detector 6 for detecting the fluorescence collected by the objective lens 3.

Between the first light source device 1 and the first scanner 2 is provided a dichroic mirror 18 for splitting off from the first laser light the fluorescence generated in the cell, collected by the objective lens 3, and returning via the dichroic mirror 17, the first scanner 2, and so forth, and directing it towards the light detector 6.

In the second light source device 15, a shutter (not shown in the drawing) that is controlled on and off by a control unit 22 (described later) is disposed in the light path of the second laser light.

The stage 5 for mounting the cells is supported by a focusing mechanism (not shown in the drawing) which moves the stage 5 in the optical axis direction.

The control unit 22 is mainly formed of a CPU (central process unit) 8, a memory 9, and a storage device 12. A sequence of process steps for implementing various functions, such as a cell-phase identifying process and an observed-image generating process to be described later, is stored in the form of a program in the storage device 12, and the CPU 8 reads out this program into the memory 9 and executes information processing or calculations, thus realizing the various functions to be described later. The CPU 8 stores in the storage device 12 data created while executing the cell-phase identifying process and the observed-image generating process mentioned above.

A frame memory 10 and an input device 13 are connected to the CPU 8 of the control unit 22. When the CPU 8 executes the observed-image generating process, the frame memory 10 buffers the constructed fluorescence image in a single frame and outputs it to a display unit 11. Thus, a fluorescence image of the cells mounted on the stage is displayed on the display unit 11.

The input device 13, including a keyboard or a pointing device such as a mouse, is mainly used for the operator to input information.

the first light source device 1, the first scanner 2, the second light source device 15, Shutters (not shown in the drawing) provided in the second light source device 15, as well as the second scanner 16 and so forth, are also connected to the CPU 8 of the control unit 22. The CPU 8 switches the laser light emitted from the first light source device 1 and controls the starting and stopping of radiation of the second laser light emitted from the second light source device 15. In addition, it also controls the irradiation position of each laser light by operating the first and second scanners 2 and 16 and so on.

The operation of the microscope apparatus A according to this embodiment, having such a configuration, will be described with reference to FIGS. 2 to 6.

First, the control unit 22 executes the cell-phase identifying process (step SA1 in FIG. 2) for identifying the cell phase of each cell mounted on the stage 5. In this cell-phase identifying process, first, with the first laser light emitted from the first light source device 1 serving as analysis laser light, the shutter provided in the second light source device 15 is put into the closed state by the control unit 22. Accordingly, in the cell-phase identifying process, only the analysis laser light emitted from the first light source device 1 irradiates the cell, whereas the observation laser light and the optical stimulus laser light are stopped.

Figure 3:
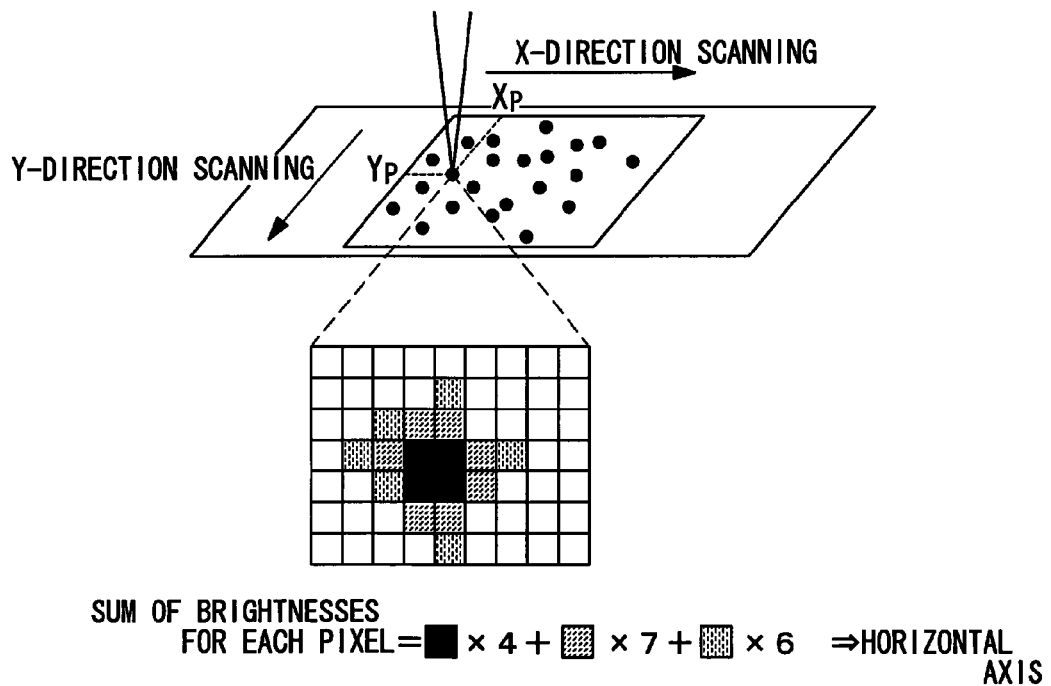
FIG. 3 is a diagram for explaining measurement of the amount of cell components in a cell-phase identifying process.

Then, the control unit 22 operates the first scanner 2. Accordingly, as shown in FIG. 3, the analysis laser light emitted from the first light source device 1 is two-dimensionally scanned (in the X-direction and the Y-direction) in the focal plane of the objective lens 3, and each cell mounted on the stage 5 is irradiated in turn. The fluorescence excited inside the cells by irradiation with this analysis light travels in the opposite direction along the same light path as the analysis laser light and is guided towards the dichroic mirror 18 via the objective lens 3, the dichroic mirror 17, and the first scanner 2. The fluorescence is split off from the analysis laser light by the dichroic mirror 18 and is guided towards the light detector 6.

In the light detector 6, the fluorescence is converted to an electrical signal and is input to the control unit 22 after being converted to a digital signal in an A/D converter 7.

The control unit 22 constructs a two-dimensional fluorescence image based on the digital signal of the input fluorescence and outputs this fluorescence image to the frame memory 13, thus displaying it on the display unit 11. The cell phase of each cell is identified using information in this fluorescence image, according to the procedure described below.

First, as shown in FIG. 3, the control unit 22 quantitatively measures the amount of cell components of the individual cells in the fluorescence image based on the brightness (light intensity) of the fluorescence. The amount of components is indicated by the total fluorescence brightness, the maximum fluorescence brightness, and so forth. The total fluorescence brightness can be obtained, for example, by summing the brightness values of the pixels that each cell occupies on the fluorescence image. The maximum fluorescence brightness can be obtained by extracting the maximum value of the brightness values of the pixels that each cell occupies in the fluorescence image.

Figure 4:
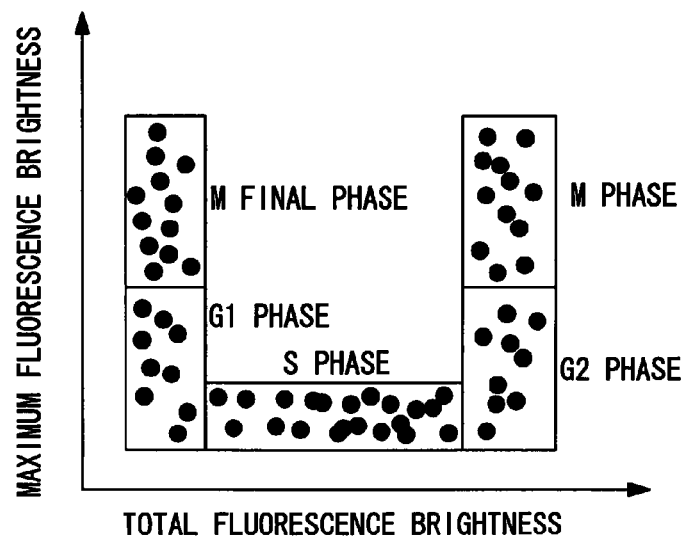
FIG. 4 shows an example of a cell-phase diagram used in the cell-phase identifying process.

Once the control unit 22 calculates the total fluorescence brightness and the maximum fluorescence brightness for the individual cells, based on the calculation result, they are plotted on coordinate axes, with the total fluorescence brightness on the horizontal axis and the maximum fluorescence brightness on the vertical axis, to create a cell-phase diagram. As a result, a cell-phase diagram such as that shown in FIG. 4 is obtained. The cell-phase diagram is statistically represented as a U-shaped graph. In this case, the control unit 22 stores the points on the cell-phase diagram and the position coordinates in the fluorescence image in association with each other.

Next, the control unit 22 divides the characteristic shape shown in the cell-phase diagram into five cell-phase regions. More specifically, the region at the top left is the M final phase, the region at the bottom left is the G1 phase, the region at the top right is the M phase, the region at the bottom right is the G2 phase, and the region between the G1 phase and the G2 phase is the S phase. Then, based on the coordinates of the individual cells in the cell-phase diagram, the cell phase of each cell is identified, and the cell phase and the position coordinates on the fluorescence image are stored in the storage device 12 in association with each other. At this time, the control unit 22 may display the cell-phase diagram on the display unit 11 together with the fluorescence image. Once saving of this information or displaying the phase diagram is completed, the control unit 22 terminates the cell-phase identifying process.

Figures 5, 6:
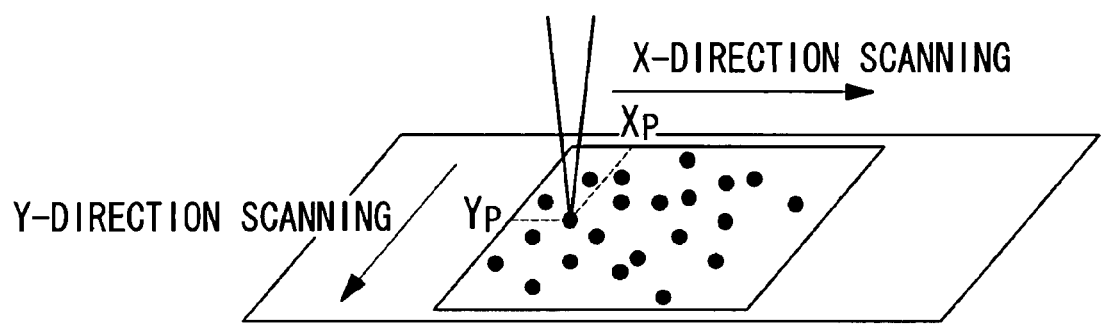
FIG. 5 is a diagram showing an example of an input box.
FIG. 6 is a diagram for explaining optical stimulation.

Next, the control unit 22 displays on the display unit 11 a cell-identifying screen for the operator to input a condition for indicating the cells to which the optical stimulus is to be applied. In addition to displaying the fluorescence image and the cell-phase diagram described above, this cell-identifying screen also displays an input box where it is possible to specify, in terms of cell phase, the cells to which the optical stimulus is to be applied. FIG. 5 shows an example of the input box. The cell phase of the cells to which the optical stimulus is to be applied is selected n the input box shown in FIG. 5.

On the cell-identifying screen, in addition to the operator selecting a cell phase in the input box, which allows him or her to specify the cell phase to which the optical stimulus is to be applied, by individually specifying cells in the fluorescence image or the cell-phase diagram displayed on the display unit 11, it is possible to specify the actual cells to which the optical stimulus is to be applied.

Input of the condition for the cells to which the optical stimulus is to be applied on the cell-identifying screen described above is achieved by the operator operating the input device 13.

Figure 2:
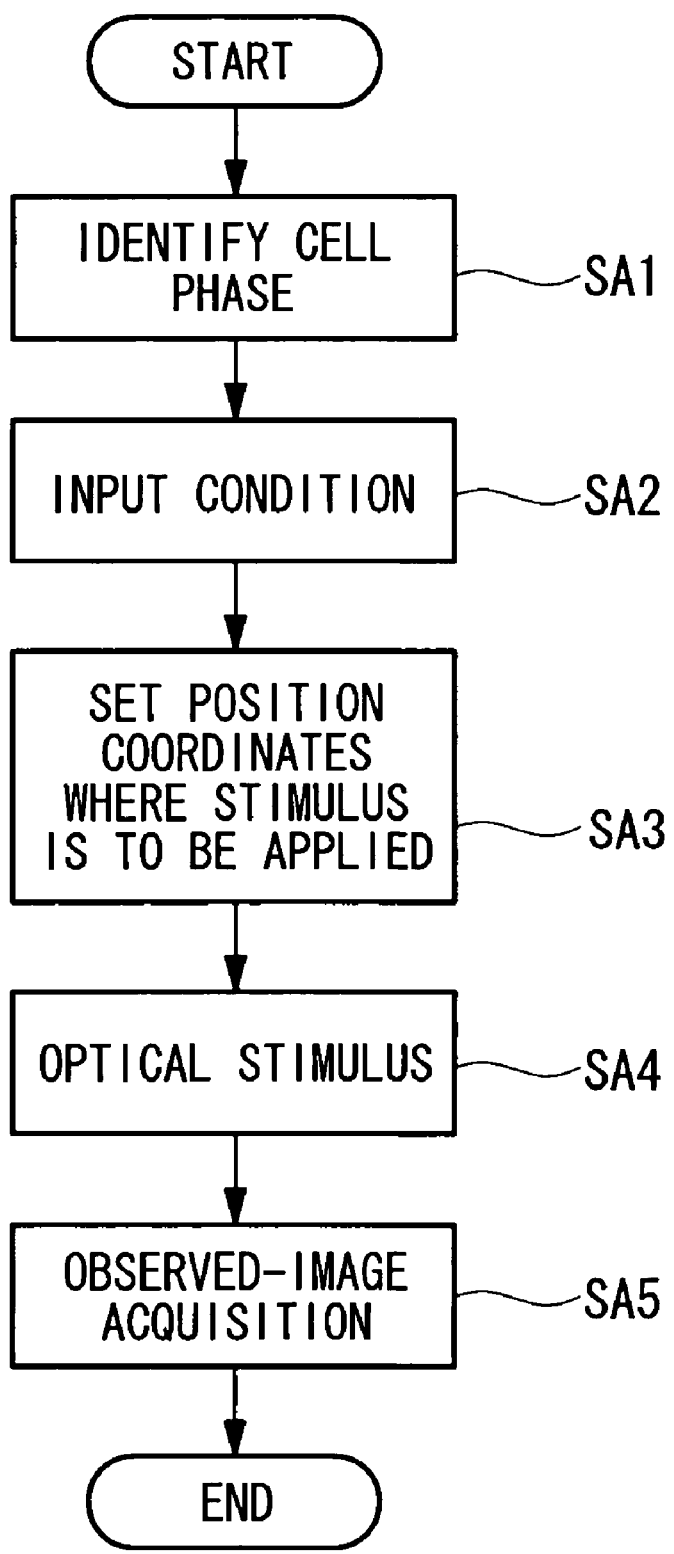
FIG. 2 is a diagram showing a procedure for a cell observation method according to the first embodiment of the present invention.

When the condition is input by the operator on the cell-identifying screen (step SA2 in FIG. 2), the control unit 22 identifies the position coordinates of the cells corresponding to this condition and sets them as the position coordinates for carrying out optical stimulation (step SA3 in FIG. 2). In this case, because the cell phase of each cell and the position coordinates are associated with each other in the storage device 12, it is possible to determine the position coordinates of the cells corresponding to the condition, on the basis of this association.

For example, when the input condition indicates that the optical stimulus is to be applied to cells corresponding to the M-phase, the control unit 22 extracts the position coordinates of the cells belonging to the M-phase from the storage device 12, and sets them as the position coordinates for carrying out optical stimulation.

Thus, once the position coordinates where optical stimulation is to be applied have been set, the control unit 22 executes the optical stimulation process and the observed-image acquisition process in parallel.

More specifically, the control unit 22 switches the first laser light emitted from the first light source device 1 to the observation laser light and opens the shutter provided in the second light source device 15. By doing so, the observation laser light emitted from the first light source device 1 and the stimulus laser light emitted from the second light source device 15 are multiplexed by the dichroic mirror 17 and irradiate the cells via the objective lens 3.

Next, the control unit 22 operates the second scanner 16 so that the optical stimulus laser sequentially irradiates the set position coordinates. Accordingly, as shown in FIG. 6, the optical stimulus laser light emitted from the second light source device 15 sequentially irradiates the cells at the set position coordinates (step SA4 in FIG. 2). By doing so, it is possible to change the cell activity. For example, it is possible to break down a specific protein in the cell, or to arrest or suppress the cell activity.

The control unit 22 operates the first scanner 2 in parallel with the operation of the second scanner 16. By doing so, the observation laser light emitted from the first light source device 1 is two-dimensionally scanned in the focal plane of the objective lens 3 and sequentially radiates the cells mounted on the stage 5 in turn.

The fluorescence excited in the cells by irradiation with the observation laser light travels in the opposite direction along the same light path as the observation laser light and is guided to the dichroic mirror 18 via the objective lens 3, the dichroic mirror 17, and the first scanner 2. Then, the fluorescence is split off from the observation laser light by the dichroic mirror 18 and is guided towards the light detector 6.

In the light detector 6, the fluorescence is converted to an electrical signal, which is input to the control unit 22 after being converted to a digital signal in the A/D converter 7.

The control unit 22 constructs a two-dimensional fluorescence image based on the input fluorescence digital signal, and by outputting this fluorescence image to the frame memory 10, it is displayed on the display unit 11. Accordingly, fluorescence images at the focal plane of the cells before and after irradiation with the optical stimulus, in other words, two-dimensional distributions of the fluorescence brightness of the cells before and after irradiation with the optical stimulus, are displayed as the experimental results (step SA5 in FIG. 2). Thus, by checking the image, it is possible for the operator to ascertain the state of the cells.

After the optical stimulus is applied, by repeating the cell-phase identifying process and the observed-image acquisition process one after another, it is possible, for example, to check how the cell phase of the cells to which the optical stimulus is applied has changed, and it is also possible to check the state of these cells using the fluorescence image. When the optical stimulus is to be applied in this checking process, it is possible to apply the optical stimulus to a desired cell by executing the optical stimulus mode.

As described above, with the microscope apparatus A according to this embodiment, after identifying the cell phases of the cells, the position coordinates of the cells to which the optical stimulus is to be applied are determined based on the condition specified by the operator, and the optical stimulus is applied to the cells at the set position coordinates. In addition, fluorescence images before and after the optical stimulus can be acquired in the observed-image acquisition mode which is executed in parallel with the optical stimulus mode described above.

Therefore, because the optical stimulus is applied to the desired cells, it is possible to apply an artificial stimulus to the cells, which enables the cell activity to be stimulated or arrested. Moreover, because observed images of before and after the optical stimulus are displayed on the display unit 11, the operator can observe the behavior of the cells before and after the optical stimulus.

With the microscope apparatus A according to this embodiment, because the cell phase identified in the cell-phase identifying process and the position coordinates of the cells are stored in association with each other in the storage device 12, it is possible to apply the optical stimulus selectively to cells in a desired cell phase.

In this embodiment, the control unit 22 carries out the optical stimulus process and the observed-image acquisition process in parallel; however, the optical stimulus process and the observed-image acquisition process may be carried out sequentially. For example, it is possible to acquire a fluorescence image immediately before the optical stimulus by executing the observed-image acquisition process, then to apply the optical stimulus to desired cells by executing the optical stimulus process, and then to acquire a cell image immediately after the optical stimulus by executing the observed-image acquisition process again.

In the observed-image acquisition process, a fluorescence image in which all cells mounted on the stage 5 serve as observed image is acquired; however, a configuration in which, for example, the operator can arbitrarily specify the cells to be observed is also possible. For example, after the condition for the cells to which the stimulus is to be applied is specified on the cell-identifying screen described above, by displaying on the display unit 11 an observed-cell identifying screen having the same layout as the cell-identifying screen described above, it is possible to specify the cells to be observed. Allowing the target observed cells to be specified in this way enables experiments to be carried out even more efficiently.

In this embodiment, the cell-identifying screen for identifying the cells to which the optical stimulus is to be applied is displayed after identifying the cell phase; however, it is also possible to display this cell-identifying screen upon commencing the experiment, that is, before executing the cell-phase identifying process (i.e. before step SA1 in FIG. 2). Accordingly, because it is possible to set the condition for specifying the cells to which the optical stimulus is to be applied before executing the cell-phase identifying process, once the cell-phase identifying mode ends, it is possible to quickly set the position coordinates where the optical stimulus is to be applied, which allows the experiment to be conducted more smoothly. Since it is possible to reduce the time taken until starting the optical stimulus mode and the observed-image acquisition mode after the cell-phase identifying mode ends, it is possible to reduce experimental errors caused over time.

Figure 7:
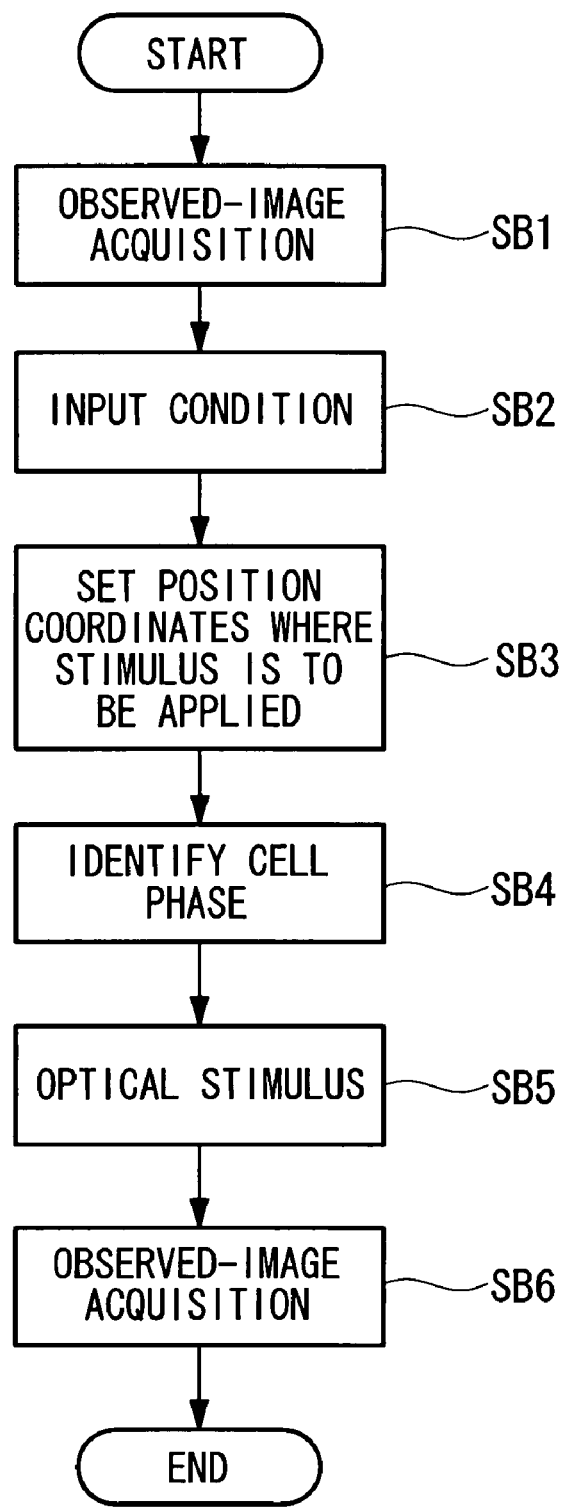
FIG. 7 is a diagram showing a procedure for a cell observation method according to another embodiment of the present invention.

As shown in FIG. 7, it is also possible, by initially executing the observed-image acquisition process, to first display the fluorescence image of the cells on the display unit 11 (step SB1) and for the operator to specify cells or a region in this fluorescence image where the stimulus is to be applied (step SB2), followed by identifying the position coordinates where the optical stimulus is to be applied based on the input condition (step SB3). In this case, the cells to which the optical stimulus is to be applied are specified as the actual cells themselves, rather than by their cell phase.

When the cells to which the optical stimulus is to be applied are specified in this way, by executing the cell-phase identifying process thereafter (step SB4), it is possible to determine the present cell phase of the cells to which the optical stimulus is to be applied and to apply the optical stimulus to the specified optical stimulus target cells (step SB5). In addition, in parallel with this optical stimulation process, it is also possible to check the state of the cells by acquiring fluorescence images before and after applying the optical stimulus by executing the observed-image acquisition process (step SB6).

In this case, cell observation may be restricted to the cells to which the optical stimulus is to be applied.

Second Embodiment

Next, a second embodiment of the present invention will be described using the drawings.

Figure 8:
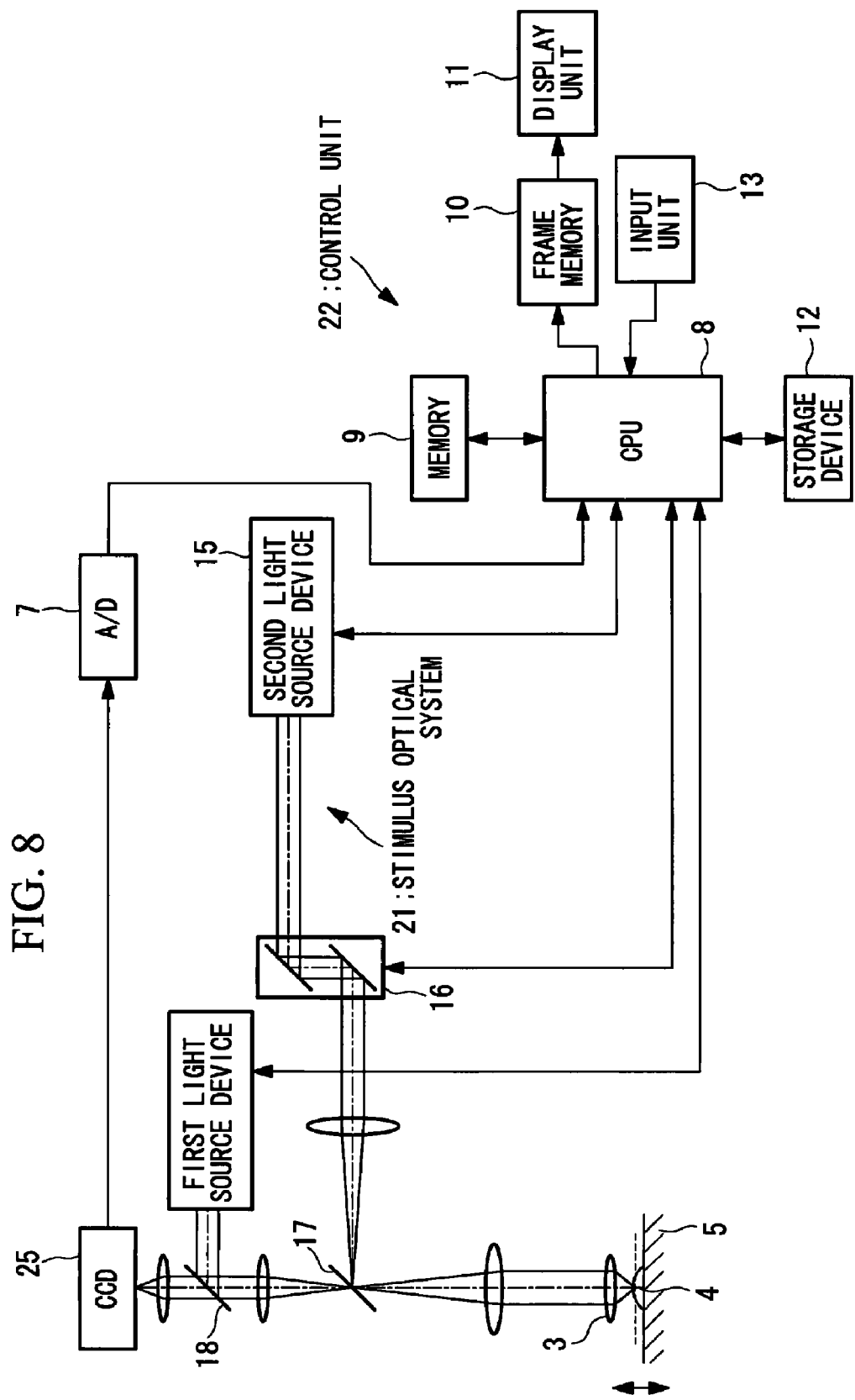
FIG. 8 is a diagram showing the overall configuration of a microscope apparatus according to a second embodiment of the present invention.

As shown in FIG. 8, the microscope apparatus of this embodiment differs from that in the first embodiment in that the fluorescence of the cells is detected with a CCD (image-acquisition unit) 25. In this figure, an illustration of the analysis/observation optical system 20 is omitted. This analysis/observation optical system 20 may be configured as a standard microscope optical system, or it may be a disk scanning optical system using a confocal disk provided with numerous minute apertures.

With this configuration, because the fluorescence excited in the cells is imaged by the CCD 25, it is possible to acquire fluorescence images at high speed.

In this embodiment, the amount of cell components of each cell, in other words, the total fluorescence brightness and the maximum fluorescence brightness of each cell, is determined using the fluorescence images acquired by the CCD 25, and the cell phase of each cell is identified by forming a cell-phase diagram based on the amount of cell components.

Third Embodiment

Next, a third embodiment of the present invention will be described using the drawings.

Figure 9:
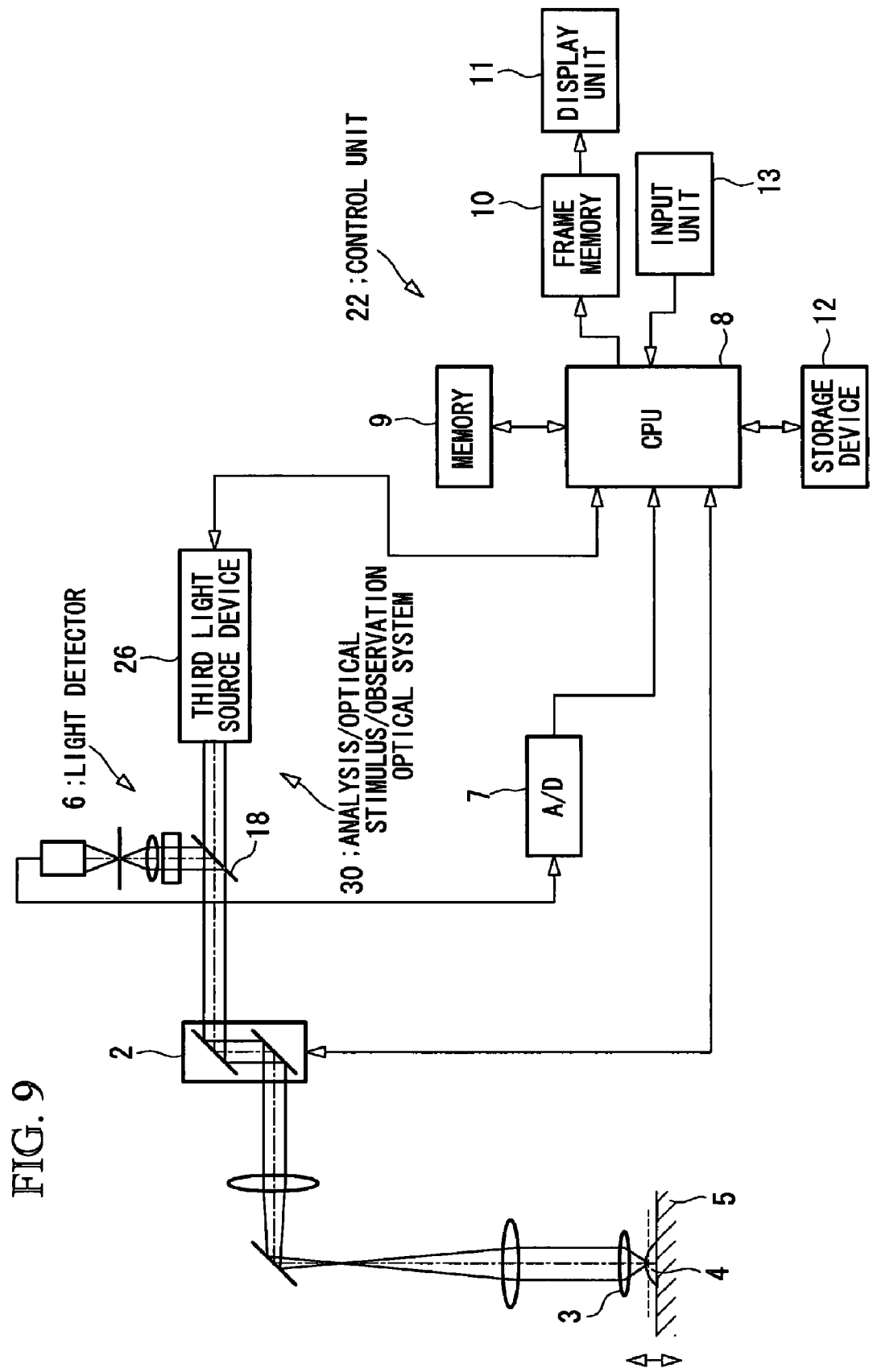
FIG. 9 is a diagram showing the overall configuration of a microscope apparatus according to a third embodiment of the present invention.

As shown in FIG. 9, the microscope apparatus of this embodiment differs from that in the first embodiment in that it is constructed using a shared optical system for the analysis/observation optical system and the stimulus optical system.

More specifically, an analysis/observation/stimulus optical system 30 according to this embodiment includes a third light source device 26 for selectively emitting one type of laser light, either analysis laser light for identifying the cell phase, observation laser light for observing the cells, or optical stimulus laser light; and a first scanner 2 which two-dimensionally moves the laser light emitted from the third light source device 26 in directions intersecting the optical axis.

Accordingly, in the cell-phase-identifying process, only the analysis laser light is emitted from the third light source device 26; in the optical stimulus process, only the optical stimulus laser light is emitted from the third light source device 26; and in the observed-image acquisition process, only the observation laser light is emitted from the third light source device 26.

As described above, with the microscope apparatus according to this embodiment, it is possible to perform identification of the cell phase, optical stimulation, and observed-image acquisition using the same optical system. Therefore, it is possible to reduce the size of the apparatus.

Fourth Embodiment

Next, a fourth embodiment of the present invention will be described using the drawings.

Figure 10:
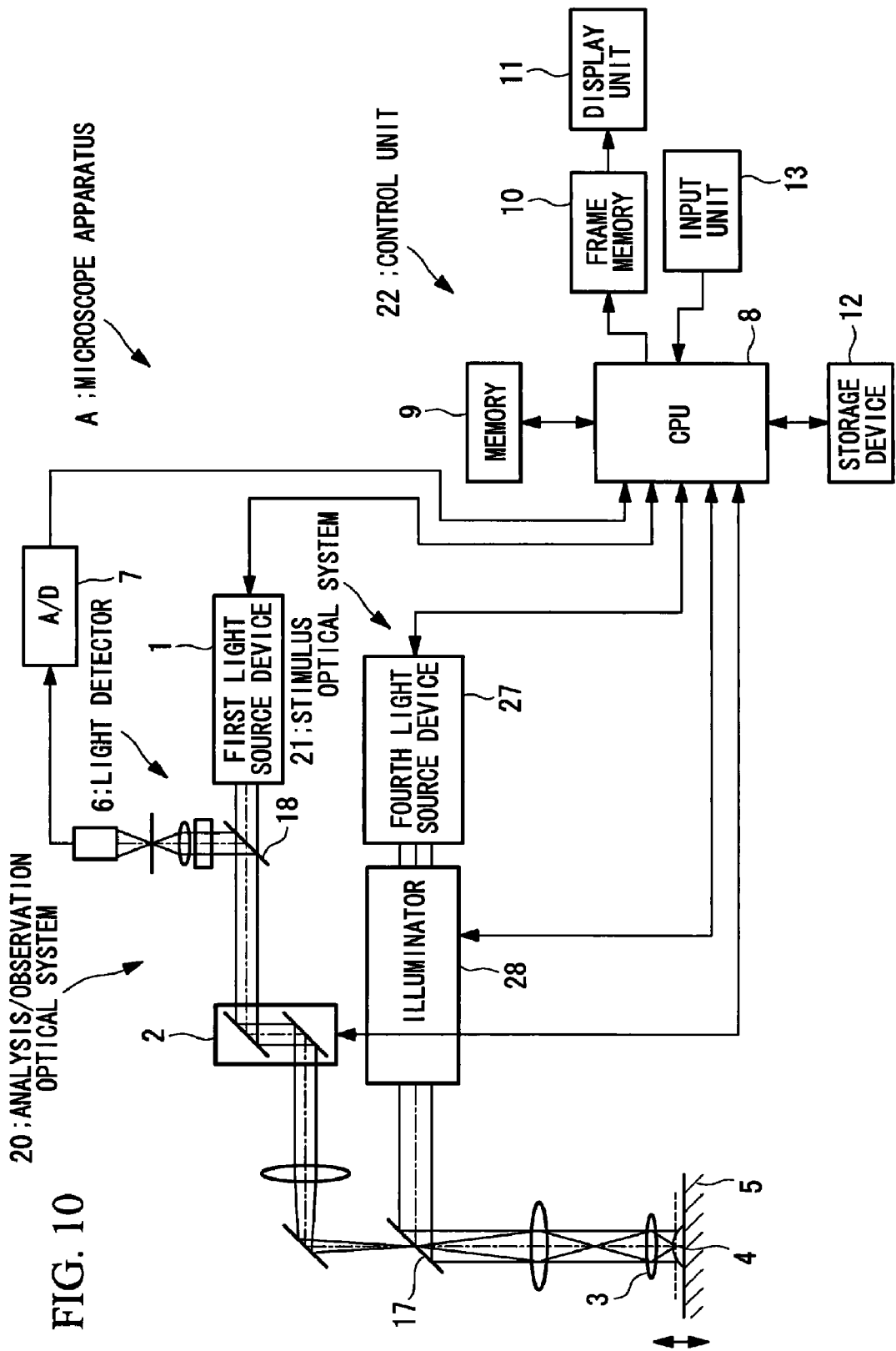
FIG. 10 is a diagram showing the overall configuration of a microscope apparatus according to a fourth embodiment of the present invention.

As shown in FIG. 10, the microscope apparatus of this embodiment differs from that in the first embodiment in that, a fourth light source device 27 for emitting light with a large beam diameter, such as a halogen lamp, is provided instead of the second light source device 15 for emitting the optical stimulus laser light, and an illuminator 28 is provided instead of the second scanner 16. The illuminator 28 is formed, for example, of a plurality of lenses disposed on the optical axis of the stimulus light emitted from the fourth light source device 27. The illuminator 28 illuminates the cells with light from a lamp light source such as a halogen lamp or a xenon lamp to perform optical stimulus, via the objective lens 3, over the entire field of view of the objective lens 3.

With this configuration, because light having a beam diameter larger than the stimulus laser light emitted from the second light source device 15 described above is emitted from the third light source device 27, it is possible to achieve effective optical stimulation over a wide area. For example, it is possible to simultaneously perform optical stimulation of a region including all of the cells. Thus, it is possible to perform optical stimulation of all cells simultaneously, which allows time-dependent response errors to be eliminated.

The microscope apparatus according to the second embodiment described above may be combined with the microscope apparatus according to the fourth embodiment described above. In other words, as shown in FIG. 10, optical stimulation may be performed with the fourth optical system 27 and the illuminator 28, and as shown in FIG. 8, the fluorescence excited by irradiating the cells with the first laser light emitted from the analysis/observation optical system may detected by the CCD 25.

In addition to the method employed in the first embodiment for identifying the cell phase, it is also possible to use, in the specimen, a fluorescence marker that visualizes the phase of the cell, and after acquiring the observed image in step SB1 in FIG. 7, to identify the cell phase of each cell by analyzing the observed image.

What is claimed is:

1. A cell observation method comprising:
identifying cell phases of cells;
applying an optical stimulus to the cells;
acquiring an observed image of the cells;
storing a position of each cell and the cell phase thereof in association with each other in a storage unit;
specifying a target cell phase for the optical stimulus; and
identifying positions of the cells in the specified cell phase using information stored in the storage unit;
wherein the optical stimulus is applied to the cells in the identified positions.

2. A cell observation method according to claim 1, further comprising:
specifying a target cell for the optical stimulus,
wherein the optical stimulus is applied to the specified cell.

3. A cell observation method according to claim 1, wherein in identifying the cell phases of the cells, illumination light for exciting fluorescence is radiated to a plurality of the cells, fluorescence generated by the cells by irradiation with the illumination light is detected, and the cell phase of each cell is identified by statistically processing a brightness of the fluorescence.

4. A microscope apparatus comprising:
a cell-phase identifying unit configured to identify cell phases of cells;
an optical stimulus unit configured to apply an optical stimulus to the cells;
an observed-image acquisition unit configured to acquire an observed image of the cells;
a storage unit configured to store a position of each cell and the cell phase thereof in association with each other;

an input unit configured to specify a target cell phase for the optical stimulus; and a cell-identifying unit configured to identify positions of cells in the specified cell phase using information stored in the storage unit, wherein the optical stimulus unit is configured to apply the optical stimulus to the cells in the positions identified by the cell-identifying unit.

5. A microscope apparatus according to claim 4, further comprising:

an input unit configured to specify a target cell for the optical stimulus, wherein the optical stimulus unit applies the optical stimulus to the specified cell.

6. A microscope apparatus according to claim 4, wherein the cell-phase identifying unit includes:

a light-radiating optical system configured to radiate illumination light for exciting fluorescence in a plurality of the cells;

a light-detecting unit configured to detect fluorescence generated by the cells due to irradiation with the illumination light; and a cell-phase analyzing unit configured to identify the cell phase of each cell by statistically processing a brightness of the detected fluorescence.

7. A microscope apparatus according to claim 4, wherein the observed-image acquisition unit includes a scanning unit configured to two-dimensionally scan observation laser light, an objective lens configured to converge the observation laser light onto a specimen and to collect observed light from the cells, generated upon irradiation with the observation laser light, a detection unit configured to detect observed light collected by the objective lens, and an image forming unit configured to form a cell image based on a detection signal from the detection unit;

wherein the optical stimulus unit includes a deflecting unit capable of adjusting a position of the optical stimulus on the cells by deflecting stimulus light in a desired direction; and wherein the stimulus light is radiated onto the specimen via the objective lens.

8. A microscope apparatus according to claim 7, further comprising a combining unit, disposed between the scanning unit and the objective lens and configured to combine the stimulus light and the observation laser light.

9. A microscope apparatus according to claim 4, wherein the observed-image acquisition unit includes an image-acquisition unit configured to detect an observed image of the cells.

10. A microscope apparatus according to claim 8, wherein the observed-image acquisition unit includes a disk-scanning optical system provided with a confocal disk having a plurality of apertures.

11. A microscope apparatus according to claim 4, wherein the optical stimulus unit includes an illuminator for illuminating the cells with light from a lamp light source.

12. A cell observation method according to claim 2, wherein in identifying the cell phases of the cells, illumination light for exciting fluorescence is radiated to a plurality of the cells, fluorescence generated by the cells by irradiation with the illumination light is detected, and the cell phase of each cell is identified by statistically processing a brightness of the fluorescence.

13. A microscope apparatus according to claim 5, wherein the cell-phase identifying unit includes:

a light-radiating optical system configured to radiate illumination light for exciting fluorescence in a plurality of the cells;

a light-detecting unit configured to detect fluorescence generated by the cells due to irradiation with the illumination light; and a cell-phase analyzing unit configured to identify the cell phase of each cell by statistically processing a brightness of the detected fluorescence.

* * * * *